United States Patent
Indira et al.

(10) Patent No.: US 6,896,911 B2
(45) Date of Patent: May 24, 2005

(54) PROCESS FOR THE PRODUCTION OF ORYZANOL ENRICHED FRACTION FROM RICE BRAN OIL SOAPSTOCK

(75) Inventors: Tyakal Nanjundiah Indira, Mysore (IN); Ayappankave Venkatadri Narayan, Mysore (IN); Rajendrakumar Suresh Barhate, Mysore (IN); Karumanchi Sreesaila Mallikarjuna Srinivasa Raghavarao, Mysore (IN); Sakina Khatoon, Mysore (IN); Gopal Channaiah, Mysore (IN); Appu Rao Gopala Rao Appu Rao, Mysore (IN); Vishweshwariah Prakash, Mysore (IN)

(73) Assignee: Council of Scientific & Industrial Research, New Delhi (IN)

( * ) Notice: Subject to any disclaimer, the term of this patent is extended or adjusted under 35 U.S.C. 154(b) by 34 days.

(21) Appl. No.: 10/400,284
(22) Filed: Mar. 27, 2003

(65) Prior Publication Data
US 2004/0192948 A1 Sep. 30, 2004

(51) Int. Cl.$^7$ .............................................. A61K 35/78
(52) U.S. Cl. ...................................................... 424/725
(58) Field of Search ............................... 424/725, 195.1

Primary Examiner—Patricia Leith
(74) Attorney, Agent, or Firm—Winstead Sechrest & Minick, P.C.

(57) ABSTRACT

The present invention relates to an improved process for the production of oryzanol enriched fraction from rice bran oil soapstock; the present invention particularly relates to saponification, dehydration and leaching of rice bran oil soapstock for production of oryzanol enriched fraction.

6 Claims, No Drawings

PROCESS FOR THE PRODUCTION OF ORYZANOL ENRICHED FRACTION FROM RICE BRAN OIL SOAPSTOCK

FIELD OF INVENTION

The present invention relates to an improved process for the production of oryzanol enriched fraction from rice bran oil soapstock. The present invention particularly relates to saponification, dehydration and leaching of rice bran oil soapstock for production of oryzanol enriched fraction.

BACKGROUND AND PRIOR ART REFERENCES

The increasing physiological benefits of oryzanol on human health have generated the interest in developing commercially viable methods for the isolation of oryzanol from its various natural sources. The beneficial nutritional effects associated with oryzanol are discussed in depth (Piironen et al., 2000, Plant sterols: Biosynthesis, biological function and their importance to human nutrition. *Journal of the science of food and Agriculture* 80, 939–966). The expansive pharmaceutical application of oryzanol include hypocholesterolemic activity (Seetharamaiah and Chandrasekhara, 1989, Studies on hypocholesterolemic activity of rice bran oil, *Artherosclerosis* 78, 219–223), The emerging application of oryzanol in cosmetic preparations includes it usefulness in treatment of skin related disorders like melanin related disorder (Tatsu et al., 1993, (Eisai Co. Ltd.) JP 05225037) and minimizing the wrinkles in aged women (Tatsu et al., 1993, (Eisai Co. Ltd.) JP 0530526). In food application, oryzanol proves its usefulness as an antioxidant (Minami and Morito, 1982. Conditions for using oryzanol and its utilization in food, *New Food Industries*, 24(10) 49–53).

In the market there is demand for a product containing 40–55% oryzanol. In addition to food, pharmaceutical and cosmetic applications as discussed above, it has application as a special diet for racehorses (McConaghy and Vetclinstud (2001) South Australian Racehorse Owners Association (ASROA) Newsletter, pp. 4). All these beneficial effects of oryzanol in health care generated interest in developing viable separation method for oryzanol from the rice bran oil soapstock. Hence there exist a need for the development of simple and cost effective method for the production of oryzanol enriched fractions. The attractive cost competent byproduct (soapstock) as starting material for value addition is major motivation for work.

Reference cannot be made to many other works since almost all the reports that are available in literature employed acidic conditions, that to, without dehydration unlike the present work. Reference can be made to only work that is available that of Rao et al., (2002) [Process for the isolation of oryzanols from rice bran oil soap stock, U.S. Pat. No. 6,410,762] which refers to a process for the isolation of oryzanol from rice bran oil soapstock comprising saponification of the oil present in the soapstock with an alkali followed by neutralization of excess alkali and conversion of soapstock into anhydrous porous soapstock noodles and subsequent extraction by suitable unit operations. This process has the disadvantages of (1) tedious pretreatment and extrusion to form noodles and subsequent dehydration of them for prolonged duration (2) High mass transfer resistance and low interfacial area during the extraction of oryzanol due to larger size of anhydrous porous soapstock noodles.

Applicants have filed a PCT application PCT/IB02/05460 on Dec. 18, 2002 which relates to a simple process for crystallization of oryzanol from oryzanol enriched fraction. The process comprising (i) nonselective temperature assisted dissolution of oryzanol enriched unsaponifiable fraction in a suitable solvent mixture; (ii) fractional precipitation of mucilaginous interfering impurities; and (iii) crystallization of oryzanol from supernatant by either single method or combination of known methods to improve selectivity of crystallization. The present invention is different from the co pending application.

At the moment, the utility of soapstock is to generate the soap for toiletries and detergent industries. Attempts in the direction for effective utilization of the byproducts of RBO refining will definitely contribute to improve the economics of RBO refining. There is need to develop a more efficient separation processes for the isolation of value added products from byproducts of RBO refining. Oryzanol in one of the important value added product from byproduct (soapstock)

OBJECTS OF THE INVENTION

The main object of the present invention is to provide an improved process for the production of oryzanol enriched fraction from rice bran oil soapstock.

Another object of the present invention is to obtain stable uniform o/w type dispersion in the soapstock.

Yet, another object of the present invention is saponification to convert neutral oil (mainly glycerides) present in the soapstock.

Still yet, another object of the present invention is dewatering/dehydration of saponified soapstock preferably by method utilizing high temperature and short time (HTST) such as drum drying.

Still yet, another object of the present invention is leaching of saponified and dehydrated soapstock for the production of oryzanol enriched fraction.

Still yet, another object of the present invention is to identify the suitable solvents or their mixtures for effective leaching of oryzanol.

Still yet, another object of the present invention is to reduce the mass transfer resistance and increase interfacial area for efficient leaching.

SUMMARY OF THE INVENTION

Accordingly present invention provides an improved process for the production of oryzanol enriched fraction from rice bran oil soap stock.

DETAILED DESCRIPTION OF THE INVENTION

Accordingly, the present invention describes a process for the production of oryzanol enriched fraction from rice bran oil soap stock, the said process comprising steps of:

a) stirring rice bran oil soap stock having moisture content in the range of 60–70% of pH ranging between 10–11 in a steam jacketed kettle at a temperature in the range of 70 to 90° C. for a period of 15 to 30 minutes to obtain an uniform dispersion, b) adding required stoichiometric amount of sodium hydroxide to the hot dispersion of step (a) mixing at a temperature in the range of 70 to 90° C. for a period of 10 to 15 minutes, c) homogenizing the hot alkaline soap stock dispersion of step (b) by passing through colloidal mixture for 3–5 passes over a period of 5–10 minutes in order to increase the surface area, d) mixing the homogenized alkaline soap stock dispersion of step (c) in a steam jacketed kettle at a temperature in the range of 70° to 90° C. for a period of 30–45 minutes for completion of saponification, e) dehydrating the saponified soap stock of step (d) by drying in an alum at a temperature in the range of 90° to 100° C., a steam pressure of 1.0–1.10 kg/cm$^2$ for a time period of less than a minute, f) leaching the saponified and dehydrated rice bran oil soap stock of step (e) in a packed bed by using an organic solvent or mixture of solvents at a temperature in the range of 25° to 29° C. for a time period of 2 hrs to 4 hrs g) decanting the leached extract of step (f), and h) desolvating the decanted extract of step (g) to obtain required oryzanol enriched fraction.

An embodiment of the present process provides the use of organic solvent selected from a group consisting of ethylacetate, acetone or mixtures thereof.

Yet another embodiment of the present process provides the use of a solvent mixture of ethylacetate and acetone.

Still another embodiment of the present process provides the use of solvent mixture of ethyl acetate and acetone in the ratio ranging between 1:4 to 1:5.

Yet another embodiment of the present process yields enriched fraction having purity up to 45%.

Still yet another embodiment of the present process provides the recovery of oryzanol enriched fraction upto 80%.

Conventional saponification reactions are carried out at elevated temperatures and for long times. Novelty of the present invention is that in contrast, in the present case it is achieved at low temperature and short time (LTST) process which enable to avoid the possible degradation of the product of interest (oryzanol). The increase in interfacial area by micromixing (by the shear force in colloidal mill) is the novelty employed here to perform the saponification pretreatment of soap stock at mild operating conditions that is, lower temperature for short duration.

Water is the impurity present in large quantity in soapstock and it is prudent to remove in the initial step itself, which considerably scales down the subsequent unit operations. The novelty employed for dewatering/dehydration by a HTST process such as drum drying, with much lesser degradation of oryzanol (drum dried soapstock has purity of 6–7% oryzanol, depending the source of soapstock).

The free form of oryzanol has higher extractability in organic solvent than its salt form. Similarly, soap (salt of FFA) does not have extractability in organic solvents. Novelty of the present invention is that the above principle is used here to produce oryzanol enriched fraction from saponified and dehydrated rice bran oil soapstock. The dehydrated soapstock by drum drying is used to reduce the mass transfer resistance and to increase the interfacial area for achieving efficient leaching. The selectivity during leaching operation is improved by performing the operation in packed bed mode (rather than in soxhlet mode).

The following examples are given by the way of illustration of the present invention and should not be construed to limit the scope of the present invention.

EXAMPLE 1

10 kg of freshly procured rice bran oil soapstock (66% moisture, pH 11.0, 6.5% oryzanol content) was mixed uniformly in a steam jacketed kettle at a temperature of 80° C. for 30 minutes in order to make the uniform dispersion. The 0.08 kg of NaOH was added to hot dispersion and mixed at a temperature of 80° C. for 15 minutes. The alkaline dispersion was passed through colloidal mill for three passes over a period of 5 minutes to obtain increased surface area. The homogenized alkaline dispersion was taken in steam jacked kettle and mixed for 30 minutes at a temperature of 80° C. in order to complete the saponification reaction. Then saponified soapstock was dehydrated by drum drying at 98° C. at a steam pressure of 1 kg/cm$^2$ over a period less than a minute.

100 g of saponified and dehydrated rice bran oil soapstcok was leached in a packed bed mode by employing 700 g of ethyl acetate as a leaching solvent for a period of 2 hours at temperature of 27° C. After leaching, extract or solvent micella was obtained by decantation which was further desolventized to obtain oryzanol enriched fraction.

The performance of the method was compared with leaching of anhydrous porous rice bran oil soapstock noodles (prepared as per Rao et al., 2002, Process for the isolation of oryzanols from rice bran oil soap stock, U.S. Pat. No. 6,410,762) under similar conditions. The results are tabulated in the following table in terms of purity and yield of oryzanol obtained after leaching.

| S.N. | Type of material | Purity of oryzanol (%) | Yield of oryzanol (%) |
| --- | --- | --- | --- |
| 1 | Drum dried soapstock, | 43 | 80 |
| 2 | Anhydrous noodles | 30 | 54 |

EXAMPLE 2

12.2 kg of freshly procured rice bran oil soapstock (66% moisture, pH 11.0, 6.5% oryzanol content) was mixed uniformly in a steam jacketed kettle at a temperature of 70° C. for 20 minutes in order to make the uniform dispersion. The 0.09 kg of NaOH was added to hot dispersion and mixed at a temperature of 70° C. for 15 minutes. The alkaline dispersion was passed through colloidal mill for four passes over a period of 8 minutes to obtain increased surface area. The homogenized alkaline dispersion was taken in steam jacked kettle and mixed for 45 minutes at a temperature of 70° C. in order to complete the saponification reaction. Then saponified soapstock was dehydrated by drum drying at 98° C. at a steam pressure of 1.1 kg/cm$^2$ over a period less than a minute.

150 g of saponified and dehydrated rice bran oil soapstcok was leached in a packed bed mode by employing 700 g of acetone as a leaching solvent for a period of 3 hours at temperature of 25° C. After leaching, extract or solvent micella was obtained by decantation which was further desolventized to obtain oryzanol enriched fraction.

The performance of the method was compared with leaching of anhydrous porous rice bran oil soapstock noodles (prepared as per Rao et al., 2002, Process for the isolation of oryzanols from rice bran oil soap stock, U.S. Pat. No. 6,410,762) under similar conditions. The results are tabulated in the following table in terms of purity and yield of oryzanol obtained after leaching.

| S.N. | Type of material | Purity of oryzanol (%) | Yield of oryzanol (%) |
|------|------------------|------------------------|----------------------|
| 1 | Drum dried soapstock, | 33.0 | 58.0 |
| 2 | Anhydrous noodles | 32.2 | 32.6 |

EXAMPLE 3

10 kg of freshly procured rice bran oil soapstock (66% moisture, pH 11.0, 6.5% oryzanol content) was mixed uniformly in a steam jacketed kettle at a temperature of 75° C. for 25 minutes in order to make the uniform dispersion. The 0.08 kg of NaOH was added to hot dispersion and mixed at a temperature of 75° C. for 15 minutes. The alkaline dispersion was passed through colloidal mill for three passes over a period of 8 minutes to obtain increased surface area. The homogenized alkaline dispersion was taken in steam jacked kettle and mixed for 30 minutes at a temperature of 80° C. in order to complete the saponification reaction. Then saponified soapstock was dehydrated by drum drying at 98° C. at a steam pressure of 1.1 kg/cm$^2$ over a period less than a minute.

50 g of saponified and dehydrated rice bran oil soapstcok was leached in a packed bed mode by employing a mixture of 262.5 g of acetone and 87.5 g of ethyl acetate as leaching solvent for a period of 3 hours at temperature of 25° C. After leaching, extract or solvent micella was obtained by decantation which was further desolventized to obtain oryzanol enriched fraction.

The performance of the method was compared with leaching of anhydrous porous rice bran oil soapstock noodles (prepared as per Rao et al., 2002, Process for the isolation of oryzanols from rice bran oil soap stock, U.S. Pat. No. 6,410,762) under similar conditions. The results are tabulated in the following table in terms of purity and yield of oryzanol obtained after leaching.

| S.N. | Type of material | Purity of oryzanol (%) | Yield of oryzanol (%) |
|------|------------------|------------------------|----------------------|
| 1 | Drum dried soapstock, | 43 | 57.3 |
| 2 | Anhydrous noodles | 30 | 45.7 |

The present process offers following advantages.

(1) Considerable reduction in scale of subsequent unit operation mainly due to fact that soapstock contains 70% moisture. In other words 100 kg of soapstock when pretreated by saponification and dehydrated will scale-down to 30 kg, thus reducing considerably the scale of subsequent unit operations.

(2) Reduction in number of unit operations and time in producing pretreated and dehydrated soapstock and the present process is much less tedious.

(3) Reduction in the degradation of oryzanol due to gentle operating conditions with respect to pH, temperature and exposure time.

(4) Enhancement in saponification due to high shear mixing provided by the homogenization, which provides the molecular level micromixing required by the saponification reaction to reach completion at mild conditions.

(5) Process is a simple, can be carried at ambient temperature & easy to scale up.

(6) Conventional soxhlet mode of extraction & associated disadvantages such as low selectivity and high cost of equipment are eliminated in present process.

(7) The mass transfer limitations during leaching process are considerably reduced by this process.

What is claimed is:

1. A process for producing an oryzanol enriched fraction from rice bran oil soap stock, the said process comprising steps:

a) stirring rice bran oil soap stock having a moisture content in the range of 60–70% and a pH ranging between 10–11 in a steam jacketed kettle at a temperature in a range of 70 to 90° C. for a period of 15 to 30 minutes to obtain an uniform hot dispersion, b) adding 0.2 to 1.2% sodium hydroxide to the uniform hot dispersion of step (a) mixing at a temperature in the range of 70 to 90° C. for a period of 10 to 15 minutes to obtain a hot alkaline soap stock dispersion, c) homogenizing the hot alkaline soap stock dispersion of step (b) by passing through a colloidal mill for 3–5 passes over a period of 5 to 10 minutes to obtain a homogenized alkaline soap stock dispersion, d) mixing the homogenized alkaline soap stock dispersion of step (c) in a steam jacketed kettle at a temperature in the range of 70° to 90° C. for a period of 30–45 minutes for saponification to obtain saponified soap stock, e) dehydrating the saponified soap stock of step (d) by drying in a rotating drum at a temperature in the range of 90° to 100° C., a steam pressure of 1.0–1.10 kg/cm$^2$ for a time period of less than a minute to obtain saponified and dehydrated rice bran oil soap stock, f) adding the saponified and dehydrated rice bran oil soap stock of step (e) to a packed bed followed by leaching the said saponified and dehydrated rice bran oil soap stock in the packed bed by using an organic solvent or mixture of solvents at a temperature in the range of 25° to 29° C. for a time period of 2 hours to 4 hours to obtain an extract, g) decanting the extract of step (f), and h) desolvating the decanted extract of step (g) to obtain the oryzanol enriched fraction.

2. The process as claimed in claim 1, wherein step (f) the organic solvent used is selected from the group consisting of ethylacetate, acetone and mixtures thereof.

3. The process as claimed in claim 2, wherein the solvent used is a mixture of ethylacetate and acetone.

4. The process as claimed in claim 3, wherein the mixture of solvent used is in a ratio ranging between 1:4 to 1:5.

5. The process as claimed in claim 1, wherein in step (h) the purity of the oryzanol enriched fraction is up to 45%.

6. The process as claimed in claim 1, wherein in step (h) the obtained oryzanol enriched fraction comprises up to 80% of oryzanol in the rice bran oil soap stock.

* * * * *